United States Patent [19]

Clynes

[11] Patent Number: 5,305,423
[45] Date of Patent: Apr. 19, 1994

[54] COMPUTERIZED SYSTEM FOR PRODUCING SENTIC CYCLES AND FOR GENERATING AND COMMUNICATING EMOTIONS

[76] Inventor: Manfred Clynes, 19181 Mesquite Ct., Sonoma, Calif. 95476

[21] Appl. No.: 931,963

[22] Filed: Aug. 19, 1992

Related U.S. Application Data

[63] Continuation-in-part of Ser. No. 793,123, Nov. 18, 1991, which is a continuation-in-part of Ser. No. 787,254, Nov. 4, 1991, Pat. No. 5,195,895.

[51] Int. Cl.$^5$ .............................................. G10L 9/02
[52] U.S. Cl. ................................... 395/2.67; 395/2.79
[58] Field of Search .................................... 381/51–53; 395/2.67, 2.79; 364/419; 84/1.03, 1.19, 1.24, 622, 626; 434/236

[56] References Cited

U.S. PATENT DOCUMENTS

| | | | |
|---|---|---|---|
| 4,763,257 | 8/1988 | Clynes | 364/419 |
| 4,999,773 | 3/1991 | Clynes | 364/419 |
| 5,029,214 | 7/1991 | Hollander | 381/51 |
| 5,195,895 | 3/1993 | Clynes | 434/236 |

*Primary Examiner*—Michael R. Fleming
*Assistant Examiner*—Michelle Doerrler
*Attorney, Agent, or Firm*—Michael Ebert

[57] ABSTRACT

A system including a touch pressure-sensitive transducer and a computer responsive thereto for producing a sentic cycle and for recording touch expression in the course of which cycle different emotions are expressed and generated by applying appropriate finger pressure to the transducer actuator. Stored in the memory of the computer is a set of words representing the different emotions, the computer being programmed to sequentially select these words at timed intervals and to audibly reproduce the selected word. Each word is followed by a series of time-spaced audible start clicks, each commanding the subject when to express with finger pressure on the transducer actuator. The signals yielded by the transducer reflecting vector components of the applied finger pressure are processed in the computer whose display terminal then presents on its screen a sentogram, the shape of which characterizes the emotion sensed by the transducer. Single or averaged sentograms developed by the subject during a particular sentic cycle are stored in the computer for comparison with those produced by the same subject in subsequent cycles to gauge the degree to which the subject's emotional responses may have changed. Stored or "live" sentograms can also be used to impart emotional content to graphically reproduced animated figures or to reproduced music modulated as a function of the sentogram, or to movement activated according to its dynamic form.

10 Claims, 1 Drawing Sheet

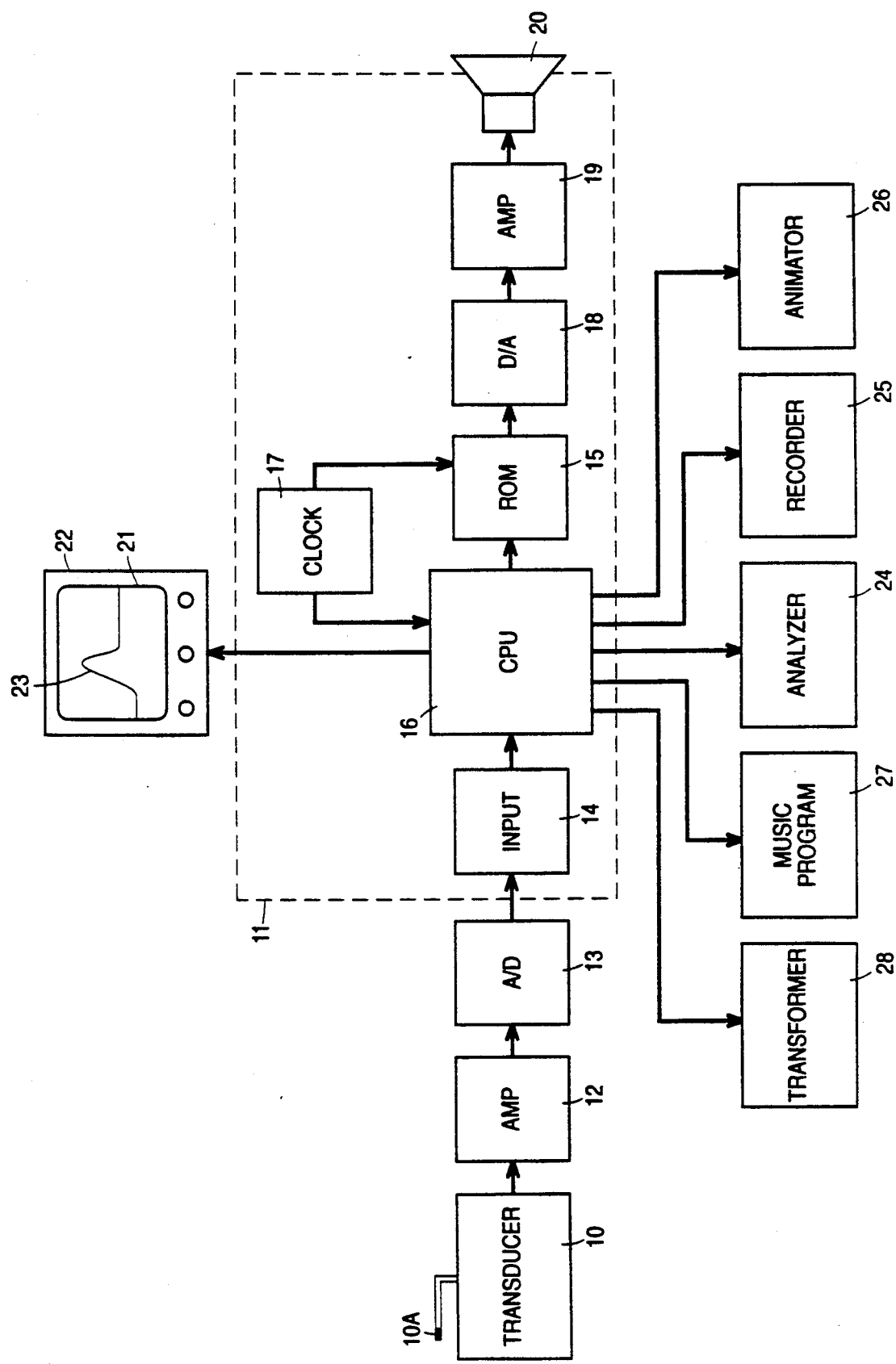

COMPUTERIZED SYSTEM FOR PRODUCING SENTIC CYCLES AND FOR GENERATING AND COMMUNICATING EMOTIONS

RELATED APPLICATION

This application is a continuation of my copending application Ser. No. 793,123, filed Nov. 18, 1991, entitled COMPUTERIZED SYSTEM FOR PRODUCING SENTIC CYCLES AND FOR GENERATING AND COMMUNICATING EMOTIONS, which in turn is a continuation-in-part of my copending application Ser. No. 787,254, filed Nov. 4, 1991, now U.S. Pat. No. 5,195,895 entitled SENTIC CYCLER UNIT, whose entire disclosures are incorporated herein by reference.

BACKGROUND OF THE INVENTION

1. Field of the Invention

This invention relates generally to a technique adapted to generate in a subject being treated different emotions which he expresses tactilely by applying finger pressure to a pressure-sensitive transducer, and more particularly to a system which includes the transducer and a computer responsive thereto for carrying out this technique, the computer being programmed to sequentially select from its memory each word in a set of words representing different emotions and to reproduce the selected word so that it can be heard by the subject who then, when commanded to do so by a series of time-spaced audible start clicks, applies finger pressure to the transducer whose output signals are processed in the computer to develop on its display terminal a sentogram, the shape of which characterizes the emotion expressed by the subject.

2. Status of Prior Art

My prior U.S. Pat. No. 3,691,652 (Clynes), entitled "Programmed System for Evoking Emotional Responses," discloses a system adapted to internally generate in a subject different emotional states in a programmed manner. By going through a timed sequence of these states in the course of a sentic cycle during which the subject applies finger pressure to a pressure-sensitive transducer in a manner expressing the emotion he then feels, the subject's ability to freely express emotion and overcome inhibitive and repressive tendencies is enhanced.

In my prior system, the programmer takes the form of a magnetic tape cassette player which reproduces at timed intervals in the course of a sentic cycle a sequence of words each donating a specific generalized emotion, such as love, hate, anger or grief. Every presented word is followed by a series of time-spaced audible start clicks commanding the subject, upon hearing each click, to express the denoted emotion by pressing with a finger the actuator element of the transducer in a manner which expresses this emotion. This transducer which senses vector components of the applied finger pressure yields output signals which are applied to a TV monitor on whose screen is displayed in real time the transient pattern or sentic shape of the subject's tactile expression of a particular emotion.

A similar system is disclosed in my U.S. Pat. No. 3,755,922 (Clynes) entitled "System for Producing Personalized Sentograms." In this system, the programmer is also a magnetic tape cassette player, but instead of presenting a sequence of words representing different generalized emotions, presented in sequence are words, each identifying an individual with whom the subject has a close relationship or about whom the subject has a distinct feeling.

In the system disclosed in my '922 patent, the transducer is coupled not only to a TV monitor as in the '652 patent, but also to an averaging device whose output represents the average of ten responses or whatever number of click-started responses is sensed for each announced name generating an emotional response. The averaged sentic shape is then recorded to produce a personalized sentogram for each name.

As pointed out in my '922 patent, the collection of personalized sentograms developed by the subject in response to a series of names is useful in characterizing his condition. Each personalized sentogram may be analyzed in the light of sentograms representing abstract, generalized emotions. For example, if the personalized sentogram for "father" is quite similar in its essentic form to an abstract sentogram for "love," clearly the subject feels love for his father. But in other instances, the personalized sentograms may exhibit compound effects, such as fear-awe or hate-anger, in which event one finds in the personalized sentograms hybrid forms of the abstract sentograms. The collection of personalized sentograms therefore lends itself to analysis to provide a personality relationship profile of the subject.

My above-identified copending application discloses a self-sufficient sentic cycler unit which dispenses with the need for a magnetic tape player as the programmer. The unit includes a solid-state memory having digitally stored therein a set of words representing different emotions, as well as a click or other command signal instructing the subject to tactilely express the emotion represented by the word selected from the memory. The memory is controlled by a programmed microprocessor associated with a clock to produce a sentic cycle in the course of which words are selected from the set in a predetermined sequence, each selected word being followed by a series of time-spaced clicks. The digital output of the memory is converted into an analog signal that is reproduced so that it can be heard by the subject. The unit is provided with a finger rest which is to be pressed by the subject, who after hearing a selected word then hears a command click in the click series following the word. After each audible click, the subject then exerts finger pressure on the finger rest in a manner expressive of the emotion generated or evoked by the word.

The unit disclosed in my copending application does not use a pressure-sensitive transducer from whose output is derived a sentogram. In that unit, finger pressure is applied by the subject to a finger rest to obtain an emotional release and other psychological benefits, and sentograms play no role in this context.

Also of prior art interest are my U.S. Pat. Nos. 4,999,773, 4,763,257 and 4,704,682 (Clynes) which disclose systems in which music is imbued with a composer's inner pulse and/or with predictive amplitude shapes embodying emotional meaning. These patents are hereinafter referred to collectively as my music processing patents.

SUMMARY OF INVENTION

In view of the foregoing, the main object of this invention is to provide a system that includes a pressure-sensitive transducer and a computer responsive to the signals yielded by the transducer for producing a sentic cycle in the course of which there are evoked in a subject being treated different emotions, each of which he seeks to express by applying finger pressure to the actuator of the transducer.

More particularly, an object of the invention is to provide a system of the above type in which the computer processes the signals yielded by the transducer so as to present on the screen of its display terminal a sentogram whose shape characterizes the emotion expressed by the subject.

A significant advantage of the invention is that the same computer also functions to average the series of sentograms produced by the subject in expressing a particular emotion, from which averaged sentogram one can determine maximum and minimum slopes, curvatures and amplitudes. These measurements, which can be also taken from single sentograms, can be compared with stored sentogram values, from which an index of similarity can be calculated to inform the subject of his condition or the progress he has made in using the system.

Another advantage of the system is that the sentograms it develops and stores can be used to impart a heightened emotional content to graphically produced animated figures or to reproduced music. Or the music produced in accordance with my music processing patents can be used with or without sentograms to visually modulate these animated figures.

Also an object of this invention is to provide means to transform a single or averaged sentogram whose shape represents a subject's emotion into a corresponding physical movement which so activates a device such as a chair, a bed or a vibrator coupled to or occupied by an individual so as to communicate this emotion to the individual.

Briefly stated, these objects are attained in a system including a touch pressure-sensitive transducer and a computer responsive thereto for producing a sentic cycle and recording touch expression in the course of which cycle different emotions are expressed and generated by applying appropriate finger pressure to the actuator of the transducer. Stored in the memory of the computer is a set of words representing the different emotions, the computer being programmed to sequentially select these words at timed intervals and to audibly reproduce the selected word. Each word is followed by a series of time-spaced audible start clicks, each commanding the subject when to express with finger pressure on the transducer actuator.

The signals yielded by the transducer which reflect vector components of the applied finger pressure are processed in the computer whose display terminal then presents on its screen a sentogram, the shape of which characterizes the emotions sensed by the transducer. Sentograms developed by the subject during a particular sentic cycle or from single expressions are stored in the computer for comparison with those produced by the same subject in subsequent cycles to gauge the degree to which the subject's emotional responses may have changed.

A stored stored sentogram derived from any expressed emotion, single or averaged, can also be useful to impart an emotional content to graphically-produced animated figures or reproduced music modulated as a function of the sentogram.

Similarly, shapes of emotional meaning derived from the computer program disclosed in my music processing patents may be used to create an animated "danse" integral with the emotion and the music. And a sentogram may be transformed into a corresponding physical movement serving to communicate the emotion expressed thereby to others.

BRIEF DESCRIPTION OF DRAWING

For a better understanding of the invention as well as other objects and further features thereof, reference is made to the following detailed description to be read in conjunction with the accompanying drawing whose single FIGURE is a block diagram of a computerized system for producing sentic cycles in accordance with the invention.

DESCRIPTION OF INVENTION

In a system in accordance with the invention, there is provided a pressure-sensitive transducer 10 having an actuator which when pressed by a finger of the subject being treated, causes the transducer to yield electrical analog signals representing vector components of the applied pressure, from which signals a sentogram is derived. These signals are applied to a digital computer 11.

In practice, the transducer may be constituted by strain gauges, force-sensitive resistors or capacitive elements adapted to sense the horizontal and vertical components of finger pressure applied to actuator 10A which may be in the form of a cantilevered finger rest. Optionally, one may also include left and right pressure-sensitive elements to produce three-dimensional sentograms defined by the pressure components in mutually perpendicular X, Y and Z directions.

The subject being treated preferably should be in a sitting position, with the transducer placed, say, on the arm rest of a chair or on a table whose level is such that the subject can extend his arm horizontally whereby he may comfortably engage the actuator with the middle finger of one hand.

In order to be able to process the transducer analog signals in digital computer 11 included in the system, they must first be converted into digital signals. For this purpose, the analog signals from transducer 10 are applied through an amplifier 12, such as one having FET stages, to an analog-to-digital converter 13 whose output is fed into an input 14 of the computer. Alternatively, the pressure-sensing element may be incorporated in an oscillator whose frequency varies as a function of the force applied to the sensing element, the frequency of the oscillator being counted to provide a digital input to the computer through an appropriate input port.

In a typical digital computer, the hardware includes a central processing unit (CPU) and a main storage unit (MS) serving to store both the program and the data on which it operates. A storage address register (SAR) holds the address of the storage location to be activated, either in order to read the contents of the location or for storing into the location. A storage data register (SDR) temporarily holds data being read into and out of storage, while an arithmetic and logic unit (ALU) performs the specified operation on the data presented at its inputs. The ALU is routed to either a register stack (RS), an I/O control unit (IOCU) or to main storage (MS) by means of signals from the central processing unit (CPU).

The register stack (RS) included in the computer is a special purpose storage unit usable for the temporary storage of data and addresses, and when put to use instead of main storage (MS) it is because it can be accessed more quickly. The I/O control unit (IOCU) represents the means which provide for the detailed control of the input/output units such as video terminals and data acquisition equipment. The instruction address register (IAR) contains the locations of the instructions currently being executed, whereas the instruction register (IR) is a temporary storage location in which the current instruction is held during execution.

The computer hardware is controlled by a series of instructions which are stored in main storage (MS), the sequence of instructions constituting the computer program.

In a system in accordance with the invention, computer 10 is preferably an integrated circuit microcomputer whose chips contain a central processing unit (CPU), a program memory (ROM), a data memory (RAM), oscillator and clock circuits, and an input/output (I/O) structure. In FIG. 1, only those elements of the computer necessary for an understanding of the system and the computer program are included. Computer 10 is programmed to respond to finger pressure applied by a subject to transducer 10 and to execute a sentic cycle.

Digitally stored at different sites in a ROM 15 or in any other computer storage facility are a set of words required for a sentic cycle lasting, say, about 30 minutes. Typically, these words are "no emotion," "anger," "hate," "grief," "love," "sex," "joy" and "reverence." Also digitally stored in ROM 15 is the sound of a start click such that as that produced by a soft knock on a piece of wood or any other abrupt sound signal acting to command the subject to apply finger pressure to the transducer actuator to physically express the emotion the subject feels that is represented by a word selected from the computer memory.

ROM 15 is controlled by a central processing unit 16 associated with a clock 17. As governed by clock 17, the computer is programmed so as to extract at predetermined intervals from ROM 15 in the course of each sentic cycle, successive words from the word set digitally stored in the ROM. Each word is followed by a series of time-spaced audible start clicks which command the subject to tactilely respond to the previously extracted word.

The digital output of ROM 15 is converted by a D-to-A converter 18 into a corresponding analog signal. This analog signal, which is in stepped form, is applied, after suitable filtering, to an amplifier 19 whose output is fed to a loudspeaker 20. Thus the subject in the course of a sentic cycle hears each word selected from the set, and following each word, the subject then hears at time-spaced intervals a series of audible command clicks.

The time spacing between clicks in a series thereof are preferably different for each emotion, but are distributed around a mean time suitably chosen for each emotion in a range of about 4 to 10 seconds. The number of clicks in the series thereof following each word representing an emotion also varies from emotion to emotion in the sentic cycle sequence, but typically lies in a range of about 20 to 40 clicks per series, though it may be less or more than that.

The sentic forms or sentograms representing an emotion expressed in terms of finger pressure by the subject are displayed on screen 21 of the computer terminal 22, the screen showing a sentic form 23.

In the sentic cycler unit disclosed in my above-identified copending application, two control buttons are provided which permit the subject to either increase the number of time-spaced clicks in the series thereof which follow a word representing a particular emotion or to skip over clicks.

When the subject at some intermediate point in the course of a click series presses the first control button, then the system reverts to the first click in the series, giving the subject an additional number of clicks to express the emotion represented by the word. But if the second button is pressed at an intermediate point in the series, then the remaining clicks are skipped and the system goes onto the next word in the sequence.

In the computerized sentic cycle system in accordance with the invention, in lieu of buttons to effect prolongation of a click series or a skipping action, the mouse associated with the computer is adapted to carry out these functions, the mouse being a mobile manual device that controls movement of a cursor on the computer display. Depression of the mouse by the subject serves to effect the desired actions. Or the computer may include a voice-actuated switching arrangement which when the user says "repeat," this will cause the click series to repeat itself, but when the user says "skip," this will then terminate the click series and go on to the next word.

The sentograms 23 displayed on screen 21 of the display terminal represent on-line sentic patterns produced each time the subject applies finger pressure to the transducer actuator in response to the series of time-spaced command clicks.

The computer is also programmed to average the successive sentograms produced in response to a series of clicks. An average sentogram has a shape which may best characterize the subject's expression of a particular emotion, for one or more of the sentograms created in a given series may constitute aberrations. The averaged sentogram is supplied to an analyzer 24 to determine maximum and minimum slopes, curvatures and amplitudes. These measurements can be compared in the analyzer with stored values. An index of similarity can be calculated from these measurements to inform the subject.

Also provided is a recorder 25 to make of record the averaged sentograms produced by a subject in the course of a sentic cycle on a particular day, so that they may be compared with those produced in subsequent sessions, thereby making it possible to gauge the subject's progress.

Observation of the sentic forms may be carried out by a trained analyst who is skilled in correlating the sentograms produced by a subject with specific states of emotion which may be "mixed states," to examine the appropriateness and significance of the expressions.

In practice, sentograms may be recorded that reflect the emotional reaction of a subject to an individual about whom he has strong feelings or to imagined situations which release a negative emotion. Thus with some individuals, the sight of a snake or a bat may give rise to an intense phobic reaction. If the objective is to desensitize the subject or get rid of a particular phobia, then by comparing the sentograms produced by the subject on a particular day with those produced on subsequent days, one may be able to gauge the progress being made by the subject toward overcoming the phobia.

The sentograms stored in the computer express an emotion such as love or anger in a sentic form that can serve to impart this emotion to various types of artistic activity. Thus with animated dancing figures created by computer-aided design techniques, a sentogram expressing a particular emotion can be so introduced into the graphics control of the animated figures as to cause the movements of the figures to express this emotion, or to change colors in corresponding dynamic ways.

Or the sentic form for a particular emotion can be used to amplitude-modulate or otherwise directly or indirectly modify the wave form of reproduced music so that the music is more expressive of this emotion. If, for example, the emotion is that of grief, the sentogram for this emotion could be used to so modulate music so as to to render it sadder. And if the emotion is that of joy, its sentogram can be used to so modulate music as to enhance the sense of joy.

It is to be understood that the musical performance which is reproduced is not devoid of emotional expression, for this depends on the nature of the music and the expressive ability of the performers. By imposing on the reproduced music aspects of the sentic form of a particular emotion, one is able to purify and/or intensify the emotion expressed by the music and heighten its effect on listeners.

In practice, the forms and corresponding parameters disclosed in my music processing patents may be substituted or combined with sentograms to create "living" dance forms that harmonize emotionally with the music and are integral therewith, thereby largely dispensing with the need for choreography.

A single or averaged sentogram stored in computer 11 representing a particular emotion expressed by a subject can be communicated to other individuals in terms of physical movement corresponding to the shape of the sentogram. With such communication, one can realize beneficial effects not heretofore attainable with known devices imparting a physical movement to an individual.

It is known to incorporate in a chair, a bed or a cradle to be occupied by an individual, an electrically-powered vibrator, the vibrations of which subject the occupant to periodic vibrations intended to relieve stress or to promote sleep. In some vibrators of this type, one can adjust the repetition rate or amplitude of the vibrations. But once an adjustment is made, the vibratory rate and amplitude remain substantially constant. Also known are vibrators which directly massage the body of an individual to relieve tension, to stimulate circulation and to obtain other beneficial effects. And in the practice of physiotherapy, a skilled masseur will so repetitively apply pressure to the body of a patient with his fingers as to relax the patient and reduce tension and stress.

But whether the massaging pressures are applied by powered vibrators or manually, they do not induce in the individual being treated an emotion serving to create a sense, say, of loving care and warmth highly conducive to the release of tension and stress. This distinction is best understood by a simple analogy. A mother, in order to soothe her baby, will repetitively stroke the baby's body with her fingers and apply a gentle pressure in such a way as to express her love for the child. This technique, which is universally practiced, is highly effective. But while it would be possible to carry out a similar stroking action by mechanical means, the impersonal pressures applied thereby would not be nearly as effective.

In the present invention, a transformer 28 responsive to a sentogram stored in computer 11 which has a shape representing an emotion to be communicated, such as love or reverence, is transformed into a corresponding physical movement of predetermined duration. To this end, the digitally-stored sentogram is converted into an analog signal which is expanded in time and then amplified and applied to an electromagnetically-operated mechanism. The armature or other movable element of the mechanism is caused to execute a movement in accordance with the shape of the sentogram.

Transformer 28 is incorporated or coupled to a chair, bed or other device to be occupied by an individual to be treated, so as to repeatedly apply the sentogram movement to the individual to be treated. Thus in the case of a seat whose back is engaged by the back of the individual, the transformer is so coupled to the chair back as to cause it to move back and forth in compliance with the shape of the sentogram.

In the case of a massaging vibrator which conventionally operates at a predetermined vibratory rate and amplitude, the motor of the vibrator will take the form of or be controlled by transformer 28 which then acts to modulate the amplitude of the periodic vibrations and/or the repetition rate thereof so that the vibratory movement then conforms to the sentogram shape.

In this way, an individual subjected to a physical movement reflecting the shape of a sentogram expressing a particular emotion will have that emotion communicated to him. And if this emotion is of a nature conducive to the release of stress or tension, its effect will be salutary.

In the case of a driver's seat in an automobile, it may be desirable at times that the emotion communicated to the occupant of this seat be such as to act as a stimulant to discourage the driver from falling asleep at the wheel. Thus the nature of the emotion communicated must be calculated to obtain the desired effect.

Speech Modulation

The invention is not limited to modulating the sounds of reproduced music with sentograms or sentic forms stored in the computer, as previously disclosed, to render the music more expressive. In practice, the reproduced sounds may take the form of speech or spoken messages digitally or otherwise stored in the computer, which are modulated by sentograms selected from the computer memory. Such modulation acts to impart to the reproduced speech the emotions represented by the selected sentograms.

In human speech, there are two distinctly different sources of sound. One source is sounds which occur during so-called "voiced" speech, such as the vowels EE, AH and AW, as well as vowel-like consonants, such as W and M. Then the vocal chord vibrations break up the flow of air from the lungs into sharp pulses. These typically occur at a repetition rate of about 75 to 250 Hz, the sounds being rich in harmonics. The other source arises from "unvoiced" consonants, such as S and F, resulting in a hiss caused by air turbulence in the mouth. In speech synthesis, one seeks to create similar sounds.

The Henderson U.S. Pat. No. 4,419,540 discloses a computer which incorporates a speech synthesizer to be used for educational purposes or as a language translator, the speech to be reproduced being digitally stored in the computer memory. Also known are computers in which speech messages are stored, which, when reproduced, supply operating instructions to the operator of the computer. Or the messages may be tied in with the computer program to guide the operator with respect to data presented on the computer display terminal. But whether the speech reproduced by the computer is for educational, instructional or for any other purpose, it has an inflexible quality. The characteristics of the reproduced speech are in no way accommodated to the personal requirements of the operator.

From an ergonomic standpoint the placement of the control elements of a computer to be manipulated by an operator must take into account his physical limitations, and consideration must be given to the ability of an operator to see illuminated data on a computer display terminal without experiencing eye fatigue. However, little consideration has heretofore been given to the psychological effects of computer-generated speech on the operator or user of of the computer.

The concern of human engineering or ergonomics is with those human characteristics that must be considered in designing a machine for human use in order that individuals and machines interact more effectively and safely. From a purely operational standpoint, the interaction between a computer and its human operator by way of reproduced speech to which the operator responds only dictates that the speech be clear and understandable. But when human engineering is applied to this interaction, the expressivity of the reproduced speech plays an important role in eliciting an effective human response to the speech and in reducing operator fatigue.

Just as a teacher whose speech is warm, friendly, and responsive is more likely to gain the attention of his students and teach them more effectively than a teacher whose voice is rigid and forbidding, an effective interaction between a computer and its operator in which the operator is required to respond to computer-generated speech messages, is promoted when this speech is not mechanical and impersonal, but is appropriately and flexibly emotionally expressive.

In a system in accordance with the invention, the reproduced sounds when in the form of speech messages issuing from a computer have flexible, emotionally-expressive qualities imparted thereto as part of a program whose character may also be selected by the operator. Thus some operators may prefer a voice that is commanding without being harsh, while others may prefer a gentler and sympathetic voice.

The sentic forms or sentograms stored in the computer may be those reflective of basic or pure emotions, and they can be those of compound or mixed emotions. The latter are produced by telescoping two component emotions (rarely three). Telescoping is effected by a seamless joining of the two component emotion forms somewhere in the middle, so that the front section of one emotion form is joined to the rear section of the second emotion. The frequency and amplitude contours of the joined together sections must connect without a frequency glitch or amplitude glitch. For this purpose, use is made of a simple short splicing function (spline), thereby avoiding slope discontinuities. Or the sentogram reflecting a compound emotion may be derived through touch by an individual expressing this emotion.

In practice, the sentic forms can be used to modulate speech in the following ways:

(a) The amplitude contour of the sentic form can modulate the amplitude contour of the speech pattern which is covered in time by the sentic form. This will affect the relative accents as well as speech portions between accents.

(b) The sentic form is placed along the speech pattern, but remains wedded to its own duration. That means that the speech pattern may be longer than the sentic form, in which case the sentic form is placed along the speech flow line in a suitable way, most frequently so that the speech ends together with the sentic form, but not necessarily so. It may also start together with it or be placed somewhere in the middle. For longer speech messages, several sentic forms would be placed along the speech flow, but not generally contiguously.

There will quite often be an interval in which no sentic form is placed, so that sentic forms will be interspersed with non-sentic speech parts, which may be fairly short, however. For very short speech flows, only a portion of the sentic form might be traversed, in which case the silence which follows is pregnant with the form, implicitly, or explicitly in terms of breathing or other "noise." A second sentic form should not be started until the previous one's duration is completed. Otherwise inhibition of feeling and frustration will tend to occur.

(c) The speech pattern needs to be modulated by the frequency curve of the sentic form; of course, synchronously with the amplitude contour of the sentic form. In this, the preexisting syntactic frequency movements (especially of the fundamental) must be preserved in altered form; i.e., within the sentic frequency modulation pattern, either by addition or by multiplication; i.e., log function, or some intermediate, non-linear function. Existing special compression and dilation techniques known in the art may be used to preserve the independence of frequency changes from the speech tempo. The timing of this is similar to (b). The amplitude of the frequency contour is largely determined by the sentic form for each emotion, and varies comparatively little with the intensity of the emotion. In addition to the frequency contour, there is an offset (DC shift) in frequency that is different for each emotion.

(d) An effective vibrato can be added to the voice in dynamically-related ways; e.g., as a dynamic function of the amplitude contour, where the vibrato is also modulated by parameters of the sentic form in its own rate as well as in its own amplitude. This is also related to the natural ten per second tremor (of muscle systems and of voice). The placement and character of the vibrato will vary for different emotions.

(e) It is desirable also for optimal effect to change the timbre of the voice. This is also done as a dynamic function of the sentic form plus a DC shift, and differently for each emotion (e.g., for love in a relaxing direction, for anger tensing). In each case, the frequency spectrum of the voice is modulated to change it transiently to correspond to the requirements of the sentic form. A VCF (voltage-controlled-filter) can be used for this purpose; several may be used to cover the required changes in the frequency bands. They too will be used in relation to the sentic form (either the amplitude or the derivative of the sentic form), or a combination of the two can be used to modulate the timbre through a VCF or other electronic means, such as variable clipping of the speech.

The vowels U, O and A are the most relaxed, I and E tense, consonants like plosives are easily tensed up; a variable treatment of consonants may be desirable for total optimization; however, much of the variation will be accounted for by the above factors alone.

(f) The parameters of the sentic form can be used to modulate the timing of the speech so that selected portions of the speech accelerate or slow down according to the dictates of the sentic form. This stretching or compressing of the speech flow as part of the expression does not affect the duration of the sentic forms, but happens within them. The slope as well as amplitude of the sentic form can be involved as a guide to the timing changes of the speech. These speed changes need to be independently realized of voice frequency changes, as mentioned in (c) supra.

The most effective expression of emotion occurs when the above-listed factors are combined. However, a graduated emotionalism can be applied to computer speech through an add-on of the various factors. For example, vibrato and timbre modulation can be added on to increase the emotionality in steps, or even frequency changes can be first left out, only the amplitude contour remaining. Thus a computer user could vary the effective intensity of emotionality displayed by the computer by simply choosing the number of add-on features to include. The computer could increase the intensity of emotion, not by increasing any factor, per se, but by the number of factors (dimensions) employed. The user could simply dial in on a speech emotion control panel "slightly emotional," "moderately emotional," "very emotional"—according to his preference or need at the time.

This may well be preferable to increasing, say, loudness or some other variable on its own. Clearly love is not expressed more effectively by greater loudness, although anger may be. Anger, however, can be effectively expressed with moderate loudness if the other variables are coordinatedly expressed. Loudness alone will not express anger unless the other factors are present also. However, as appropriately modulated whisper can express virtually all the emotions. With the coordinated shaping of emotional expression in the above-described manner, it becomes possible to produce computer-generated expressive speech exceeding in persuasiveness that of average human speech.

Moving Sound Source

By means of sentic-form modulation, a source of sound can be made to undergo movement in space, the sound source tracing out in space at an appropriate time scale, the trajectory of the sentic form. This may be realized either by actual movement of a single sound source in accordance with the sentic form or as an auditory effect produced through several stationary speakers at different spatial positions, the sentic-form modulation of the sounds produced by the respective speakers being coordinated in well-known ways as in stereophonic systems.

Sound movements in accordance with the sentic form will act to communicate the corresponding emotional quality in one listener, thereby enhancing the emotional communication in an additional modality. This would be enhancing for cinema, television and for stage performances, especially for disembodied speech.

While there has been shown and described a preferred embodiment of a computer system in accordance with the invention, it will be appreciated that many changes and modifications may be made therein without, however, departing from the essential spirit thereof. Thus sentograms can be obtained from other modalities as from brain functions directly.

I claim:

1. A computer system in which the sounds of speech are stored and reproduced, the reproduced sounds being emotionally expressive, said system comprising:
    (a) a computer provided with a memory in which the sounds are stored, and including means to reproduce the sounds;
    (b) a set of sentograms stored in the computer having respective wave forms expressive of different emotions, each sentogram being derived through touch from an individual expressing a particular emotion; and
    (c) means to amplitude modulate the sounds of speech to be reproduced in accordance with a dynamic function of the amplitude contour of a sentogram selected from the set to impart emotional expressivity thereto that reflects the emotion felt by the individual, said sounds being the sounds of speech messages stored in the computer, said system including means to select a speech message to be reproduced.

2. A system as set forth in claim 1, in which each sentogram reflects a basic emotion.

3. A system as set forth in claim 1, in which each sentogram reflects a compound emotion formed by combining at least two basic emotions.

4. A system a set forth in claim 1, in which the speech message to be reproduced is frequency-modulated in accordance with the frequency contour of the sentogram.

5. A system as set forth in claim 1, further including means to add tremor or vibrato to the reproduced speech message as a dynamic function of the sentogram.

6. A system as set forth in claim 1, including means to change the timbre of the reproduced speech message as a dynamic function of the sentogram.

7. A system as set forth in claim 1, including means to modulate the timing of the speech message so that selected portions thereof accelerate or slow down 8. A system as set forth in claim 1, further including means to convert the sentogram into a spatial trajectory of a sound source.

9. A system as set forth in claim 8, wherein said sound source is caused to move in accordance with the shape of the sentogram.

10. A system as set forth in claim 8, further including a plurality of speakers at different spatial positions, the modulation of the sounds produced by the respective speakers being coordinated to create an auditory effect of apparent movement.

* * * * *